United States Patent
Fujii et al.

(10) Patent No.: US 8,906,451 B2
(45) Date of Patent: Dec. 9, 2014

(54) METHOD FOR PRODUCING COATED WATER-SOLUBLE PARTICLES

(75) Inventors: Hiroyuki Fujii, Ube (JP); Nobuhiro Okada, Ube (JP); Hideaki Sueta, Ube (JP); Tadashi Tanaka, Ube (JP); Kazuyoshi Morita, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 118 days.

(21) Appl. No.: 13/500,267

(22) PCT Filed: Oct. 5, 2010

(86) PCT No.: PCT/JP2010/067447
§ 371 (c)(1),
(2), (4) Date: Apr. 4, 2012

(87) PCT Pub. No.: WO2011/043335
PCT Pub. Date: Apr. 14, 2011

(65) Prior Publication Data
US 2012/0198898 A1    Aug. 9, 2012

(30) Foreign Application Priority Data

Oct. 6, 2009   (JP) ................. 2009-232182
Feb. 1, 2010   (JP) ................. 2010-020182
Sep. 22, 2010  (JP) ................. 2010-212340

(51) Int. Cl.
| | | |
|---|---|---|
| C05C 9/00 | (2006.01) | |
| C05G 3/00 | (2006.01) | |
| A01N 25/26 | (2006.01) | |
| B05D 7/24 | (2006.01) | |
| C05C 1/00 | (2006.01) | |
| C05C 5/02 | (2006.01) | |
| C05B 7/00 | (2006.01) | |
| C05B 3/00 | (2006.01) | |
| C05D 1/00 | (2006.01) | |
| C05D 9/00 | (2006.01) | |
| C05F 11/00 | (2006.01) | |

(52) U.S. Cl.
CPC .............. *C05G 3/0029* (2013.01); *A01N 25/26* (2013.01)
USPC ............ 427/217; 71/11; 71/28; 71/29; 71/30; 71/33; 71/34; 71/50; 71/51; 71/53; 71/58; 71/60; 71/63; 71/64.07

(58) Field of Classification Search
USPC ............. 71/11, 28–30, 33, 34, 50, 51, 53, 58, 71/60, 63, 64.07; 427/214
See application file for complete search history.

(56) References Cited

U.S. PATENT DOCUMENTS 3,475,154 A * 10/1969 Kato .......................... 71/64.07
4,772,490 A    9/1988 Kogler et al.
(Continued)

FOREIGN PATENT DOCUMENTS

AU    B-12282/97    1/1997
DE    35 44 451 C1  1/1987
(Continued)

OTHER PUBLICATIONS

German Office Action with English translation dated May 22, 2013 (eight (8) pages).
(Continued)

*Primary Examiner* — Wayne Langel
(74) *Attorney, Agent, or Firm* — Crowell & Moring LLP (57) ABSTRACT

A method for producing coated water-soluble particles in a manner to form two or more coating layers on surfaces of the water-soluble particles, characterized by including: a step A wherein after supplying a first coating material that contains a polyol component and an isocyanate component, a second coating material is additionally supplied to surfaces of first coating bodies that have coating layers formed of the first coating material that has not been sufficiently cured, so that second coating bodies that are provided with coating layers of the second coating material are obtained.

8 Claims, 1 Drawing Sheet

(56) References Cited

U.S. PATENT DOCUMENTS

| | | | |
|---|---|---|---|
| 5,399,186 A | * | 3/1995 | Derrah et al. ............ 71/64.02 |
| 5,547,486 A | * | 8/1996 | Detrick et al. ............ 71/28 |
| 6,176,891 B1 | | 1/2001 | Komoriya et al. |
| 6,364,925 B1 | | 4/2002 | Markusch et al. |

FOREIGN PATENT DOCUMENTS

| | | |
|---|---|---|
| JP | 4-305085 A | 10/1992 |
| JP | 7-500560 A | 1/1995 |
| JP | 9-202683 A | 8/1997 |
| JP | 10-291881 A | 11/1998 |
| JP | 2000-44377 A | 2/2000 |
| JP | 2001-213685 A | 8/2001 |

OTHER PUBLICATIONS

Corresponding International Search Report with English Translation dated Dec. 14, 2010 ( four (4) pages).

Form PCT/ISA/237 (five (5) pages).

\* cited by examiner

METHOD FOR PRODUCING COATED WATER-SOLUBLE PARTICLES

TECHNICAL FIELD

The present invention relates to a method for coating water-soluble particles.

BACKGROUND ART

In recent years, there have been required a fertilizer, an agricultural chemical and a method for using them, which are of an advanced labor-saving type and high in efficiency, in view of; environmental impact of the leaching of components released from a particulate fertilizer, a particulate agricultural chemical or the like; labor-saving associated with aging farmers; and the like. By way of the above background, various fertilizers and agricultural chemicals of a controlled-release type have been proposed and applied to practical use.

Coated particles are formed by coating the surface of the particulate fertilizer or the particulate agricultural chemical with an organic or an inorganic coating material thereby controlling release of its interior components. Particularly, coated particles formed by using an organic coating material such as resin are superior in release-controlling function, so that such a type occupies the mainstream of the coated fertilizer and the coated agricultural chemical.

Resin used as the coating material are various but a thermosetting resin such as a urethane resin is widely applied because of its strength as a coating, good resistance to water, easiness of release-property control, applicability without solvent and the like.

In patent document 1, there is disclosed a coated granulated fertilizer formed by coating a granulated fertilizer with a reaction product of polyhydroxyl compound constituted of one kind of wool grease recovered in the case of washing wool, lanolin, lanolin fatty acid and lanolin alcohol or the mixture thereof and polyisocyanate. It is proposed to control the release by repeating a coating step, an organic-solvent spraying step and an evaporation step.

In patent document 2, there is disclosed a process for manufacturing membrane-covered fertilizer granules by applying layers of a polyisocyanate and a polyol, and more specifically, a process for manufacturing fertilizer granules to which coating materials are applied at such a ratio that each of the layers has a thickness of 10 to 30 μm, preferably 15 to 20 μm. It is proposed to control the release by repeating resin application, mixture, amine application and aeration.

Additionally, in patent document 3, there is disclosed a method for producing a granular coated fertilizer coated with a thermosetting resin, in which the following steps (1) to (5) are carried out in the order thereby producing a granular fertilizer free from defect in application: (1) a step of bringing the granular fertilizer into a rolling state; (2) a step of adding an uncured liquid thermosetting resin to the granular fertilizer which is under the rolling state, in an amount capable of providing 1 to 10 μm film thickness; (3) a step of coating the surface of each of fertilizer granules with the uncured thermosetting resin while keeping the rolling state of the granular fertilizer; (4) a step of curing the uncured thermosetting resin while keeping the rolling state of the granular fertilizer; and (5) a step of repeating the steps (1) to (4) one or more times. Incidentally, this patent document discloses that the film thickness is required to be 10 μm or lower, since aggregated granules consisting of myriad granules and formed such that the resin is so increased in adhesion property as to adhere the fertilizer granules to each other damages the surface of the resin.

Furthermore, there is set forth in patent document 4 a method for producing polyurethane encapsulated, sustained release fertilizer particles, including (1) a step of applying an isocyanate-reactive component containing a polyesterether polyol to fertilizer particles to form coated fertilizer particles and (2) a step of applying a polyisocyanate component onto the coated fertilizer particles from the step (1) to form polyurethane encapsulated fertilizer particles. These steps may be continuously repeated a required number of times in the use of the polyurethane encapsulated fertilizer particles of the step (2) instead of the fertilizer particles of the step (1) so that: polyurethane encapsulated fertilizer particles containing about 2 to 20 weight % of polyurethane relative to the total weight of an encapsulated fertilizer composition is formed; and polyurethane constituting the polyurethane encapsulated fertilizer particles absorb a water content of less than 1 weight % relative to the total weight of the polyurethane encapsulated fertilizer particles.

PRIOR ART DOCUMENTS

Patent Documents

Patent Document 1: Japanese Patent Application Publication No. 4-305085
Patent Document 2: Japanese Patent Application Publication No. 7-500560
Patent Document 3: Japanese Patent Application Publication No. 9-202683
Patent Document 4: Japanese Patent Application Publication No. 2001-213685

DISCLOSURE OF THE INVENTION

Problems to be Solved by the Invention

In the process of manufacturing the coated water-soluble particles by using a thermosetting resin, there has been a drawback of defects caused on the surfaces of the coated water-soluble particles.

Moreover, a mass production in a big facility such as a plant has raised a problem of causing more defects on the surfaces of the coated water-soluble particles, unlike the case of a small production in a small laboratory apparatus.

In view of the above problem, for the purpose of preventing the above-mentioned defects of the surfaces of the coated water-soluble particles, the conventional techniques have had no choice but to carry out the addition of the coating material two or more times to increase the thickness of the coating layers.

The method of patent document 1 uses an organic solvent, and therefore not only the coating step is complicated to increase the production time but also a great caution is required in respect of toxicity, flammability etc. during production. Additionally, it has a problem of necessity to conduct complicated operations in order to remove and recover the organic solvent, since an insufficient removal of the organic solvent adversely affects the environment.

Furthermore, in the method of patent document 2, there is performed an amine mist application in addition to the resin application, and therefore not only the coating step is complicated to increase the production time but also a great caution is required in respect of toxicity, flammability etc. during production. Additionally, it has a problem of necessity to conduct complicated operations in order to remove and recover the amine mist, since an insufficient removal of amine mist adversely affects the environment.

Furthermore, the method of patent document 3 repeats the addition of a small quantity of the coating material to the particulate fertilizer, and therefore there are a problem of increasing the thickness of the coating layers and a problem of so increasing the production time as to reduce productivity.

Moreover, the method of patent document 4 repeats the three steps (i.e. the addition of polyesterether polyol to the each coating, the addition of the polyisocyanate component to the same, and drying) and therefore possesses a problem of so increasing the production time as to reduce productivity.

An object of the present invention is to provide a method for producing coated water-soluble particles, by which the thickness of coating layers can be reduced and defects on the surfaces of the coating layers are reduced, the method requiring no cumbersome operations and shortening the production time thereby enabling mass production.

Means for Solving the Problems

A thermosetting resin loses flowability and increases its adhesion property, as its thermosetting reaction develops by heat. Accordingly, water-soluble particles, each of which is coated with the thermosetting resin, are adhered to each other at the thermosetting resin formed on each surface. Then, the particles are adhered to each other to form aggregated particles. As a result of the inventors' eager studies, it has been found that the defects as mentioned above are caused when the coating layers adhered to each other are unstuck or when the coating layers are brought into contact with or adhered to an apparatus for maintaining a flowing or rolling state thereby bringing about a peeling or wearing on the coating layers. Furthermore, it became evident that, in the case where the thermosetting resin is a urethane resin, a coating material for forming another coating layers is applied onto coating layers in which the thermosetting reaction is not sufficiently developed thereby making it possible to obtain coated water-soluble particles whose defects as discussed above are improved as compared with the conventional coated water-soluble particles, which is surprising.

More specifically, the present invention is a method for producing coated water-soluble particles in such a manner as to form two or more coating layers on surfaces of the water-soluble particles. This method is characterized by including a step A wherein after supplying a first coating material that contains a polyol component and an isocyanate component, a second coating material is additionally supplied to surfaces of first coating bodies that have coating layers formed of the first coating material that has not been sufficiently cured, so that second coating bodies that are provided with coating layers of the second coating material are obtained.

The above-mentioned step A may be repeated two to ten times to form two to ten coating layers. The two or more coating layers may be formed by continuously conducting a supply of new coating materials under a condition where an antecedent coating material is insufficiently cured. For example, a new coating material is supplied to the surfaces of coating bodies that have coating layers formed of a supplied coating material that has not been sufficiently cured, and a further coating material is supplied to the surfaces of coating bodies that have coating layers formed of the coating material that has not been sufficiently cured.

The above-mentioned first coating material contains at least a polyol component and an isocyanate component and may be a material liquid for forming coating layers in which thermosetting is insufficient. Additionally, the coating layers refer to layers for coating the surfaces of the water-soluble particles and the surfaces of the above-mentioned coating bodies, and may refer to either or both of coating layers in which thermosetting is sufficient and those in which thermosetting is not sufficient.

The first coating bodies are provided such that coating layers where thermosetting is not sufficient are formed at least on the surfaces, in which another coating layers may be formed on the inner side of the coating layers formed on the surfaces. Additionally, coating layers in which thermosetting is not sufficient may be directly formed on the surfaces of the water-soluble particles.

The method for producing coated water-soluble particles, according to the present invention is characterized in that the second coating material contains a polyol component and an isocyanate component.

Moreover, the second coating bodies are provided in such a manner as to supply the second coating material to the surfaces of the first coating bodies to form coating layers. In the case where the second coating material contains a polyol component and an isocyanate component, the coating bodies may refer to either or both of coating layers in which thermosetting is sufficient and those in which thermosetting is insufficient; however, in the case of repeating the step A, it is preferable that the second coating bodies have at their surface coating layers in which thermosetting is not sufficient.

Furthermore, the method for producing coated water-soluble particles, according to the present invention is characterized by starting the supply of the second coating material within a time range represented by $T_x$ that satisfies the following relational expression:

$$0.5 \leq (T_x - T_0)/(T_a - T_0) \leq 3.0$$

where: $T_0$ is a time at which, after finishing the supply of the first coating material, the first coating bodies begin adhering to each other to form aggregated particles; and $T_a$ is a time at which the volume of the aggregated particles reaches maximum.

"The volume of the aggregated particles" refers to an apparent volume of the aggregated particles consisting of the coating bodies adhered to each other through the coating layers disposed at the surfaces of the coating bodies. The coating bodies are visually observed. Additionally, it is supposed that the adhesion property of the coating layers disposed at the surfaces of the coating bodies reaches maximum when the volume of the aggregated particles reaches maximum. Some time after the supply of the first coating material is completed, the first coating material is changed to the first coating bodies formed having at their surface coating layers in which thermosetting is not sufficient. Then, the coating bodies begin adhering to each other to form the particles, upon which the volume of the aggregated particles begins to increase (a time taken therefor is represented by $T_0$).

Moreover, the second coating material may be preferably supplied in its substantially whole quantity, within a time range represented by $T_x$. "Substantially whole quantity" refers normally to 90% or greater of the second coating material which should be added during this operation, preferably 98% or greater of the second coating material which should be added during this operation. Much more preferably, the whole quantity of the second coating material which should be added during this operation is supplied within the above time range and not supplied out of the above time range.

Furthermore, the method for producing coated water-soluble particles, according to the present invention is characterized by starting the supply of the second coating material within a time range represented by $T_x$ that satisfies the following relational expression:

$$0.5 \leq (T_x - T_0)/(T_a - T_0) \leq 2.0.$$

Furthermore, the method for producing coated water-soluble particles, according to the present invention is characterized in that the first coating material and the second coating material contain an amine compound.

Furthermore, the method for producing coated water-soluble particles, according to the present invention is characterized in that the mass of the coating layers, per one layer, is 0.5 to 5 mass % relative to the mass of the coated water-soluble particles.

Furthermore, the method for producing coated water-soluble particles, according to the present invention is characterized in that the water-soluble particles have a particle diameter of from 1 to 10 mm.

Effects of the Invention

The method for producing coated water-soluble particles, according to the present invention allows reducing defects in the surfaces of the coating layers, shortening the production time, and decreasing the thickness of the coating layers as a whole. Additionally, one preferable example of the present invention does not need cumbersome operations for removing and recovering a solvent because the solvent is not used therein. Moreover, one preferable example of the present invention can provide the quality with stability and can resist mass production.

MODES FOR CARRYING OUT THE INVENTION

Hereinafter, a preferable example of the present invention is discussed. In the present invention, a first coating material that contains a polyol component and an isocyanate component is supplied to water-soluble particles which is in a flowing or rolling state while maintaining the flowing or rolling state to form first coating bodies that have coating layers in which thermosetting is not sufficient. Then, a second coating material is supplied thereto to form second coating bodies that have coating layers in which thermosetting is not sufficient. After providing a desired number of layers in which thermosetting is not sufficient so that the above-mentioned first and second coating bodies are formed, the water-soluble particles as a whole are so heated as to sufficiently cause thermosetting.

In the case of forming new coating layers on the surfaces of the first coating bodies, a time $T_x$ to start supplying the second coating material preferably satisfies the following expression, as discussed above:

$$0.5 \leq (T_x - T_0)/(T_a - T_0) \leq 3.0,$$

and more preferably, $$0.5 \leq (T_x - T_0)/(T_a - T_0) \leq 2.0.$$

If $T_x$ is less than 0.5, the supply of the second coating material is started under a condition where the formation of the coating layers formed by supplying the first coating material is not sufficient, so that a good release property is sometimes not obtained. Meanwhile, if $T_x$ exceeds 3.0, the coating layers formed by supplying the first coating material causes thermosetting more and more so as to once form aggregated particles. Since the coating layers begin to encounter peeling or the like after this, defects are increased and a good release property is sometimes not obtained.

Figure 1:
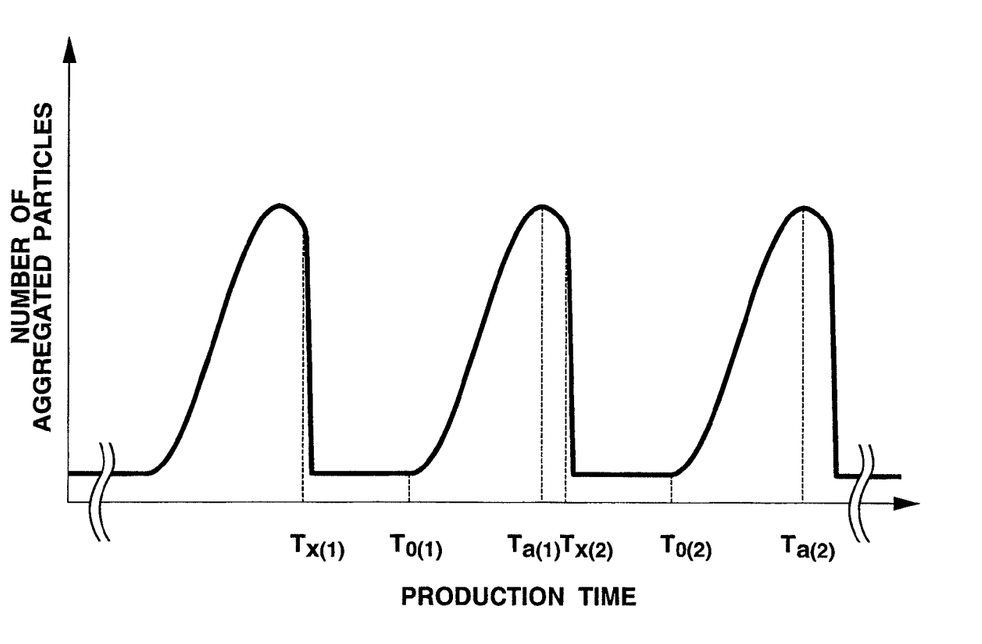
FIG. 1 is a diagram showing an example of a relation between the production time and the volume of the aggregated particles.

Referring now to FIG. 1, the above-mentioned $T_x$ will be explained below. The drawing schematically illustrates an example of a relation between the production time and the volume of the aggregated particles in the step A, and represents a time at which the first or second coating bodies begin to form the aggregated particles after the supply of the first or second coating material is completed, by $T_{0(1)}$ or $T_{0(2)}$. $T_{a(1)}$ or $T_{a(2)}$ represents a time at which the volume of the aggregated particles of the first or second coating bodies reaches maximum. $T_{x(1)}$ or $T_{x(2)}$ represents a time to begin supplying the first or second coating material. Incidentally, the above-mentioned expression $(T_x - T_0)/(T_a - T_0)$ is also expressed as follows:

$$(T_{x(2)} - T_{0(1)})/(T_{a(1)} - T_{0(1)}).$$

After supplying the first coating material, the supplied first coating material begins to gradually increase in viscosity, so that adhesion between the first coating bodies and an apparatus or that between the first coating bodies and the first coating bodies through the coating material is started. At the moment of $T_0$, the first coating bodies are adhered to each other, and additionally aggregated particles consisting of the first coating bodies that keep adhesion and do not leave from each other even in a flowing or rolling state begin to be confirmed.

After undergoing the state of $T_{0(1)}$, the volume of the aggregated particles grows more and more. Then, at the moment of $T_{a(1)}$ where the apparent volume reaches maximum, the viscosity of coating layers formed at the surfaces of the aggregated particles and insufficient in thermosetting reaches maximum. Furthermore, after undergoing the state of $T_{a(1)}$, the aggregated particles begin breaking little by little and the volume of the aggregated particles begin to decrease. Incidentally, if the thermosetting is further developed without supplying the second coating material after the state of $T_{a(1)}$, the coating layers formed at the surface become impaired due to friction between the first coating bodies and the apparatus, peeling between each of the first coating bodies or the like.

Moreover, a time $T_{x(2)}$ to start supplying the second coating material may come before $T_{a(1)}$ so long as it comes within the range obtained by the above-mentioned expression, though it lies after $T_{a(1)}$ in FIG. 1. When the second coating material is supplied at $T_{x(2)}$, the second coating material whose viscosity is low for the moment is embedded between the first coating bodies and the first coating bodies having been adhered to each other thereby allowing a prompt breakage of the aggregated particles With this, it becomes possible to abruptly reduce the volume of the aggregated particles. In this case, the surfaces of the first coating bodies are to be coated with the second coating material before encountering damages due to thermosetting, upon which the second coating bodies are to be formed.

In bringing the water-soluble particles into the flowing or rolling state, the water-soluble particles are preheated by hot wind or the like for a certain period of time. On this occasion, a preheat time and preheat temperature may be suitably arranged so long as the water content of the water-soluble particles is such an extent as not to affect the used coating material, i.e., the first and the second coating materials and the like, and so long as the temperature of the water-soluble particles becomes the coating temperature.

The coating temperature is normally from the ordinary temperature (about 25° C.) to 150° C., preferably from about 40 to about 100° C., and is suitably selected according to the formation time, the composition ratio of the coating material to be used, the kind of the water-soluble particles to be used. In the case of water-soluble particles that contain a component easily decomposable or modifiable by heat, it is necessary to perform coating at relatively low temperatures. For example when urea is used as the water-soluble particles, coating is preferably conducted at temperatures not higher than 90° C.

It is possible to use an apparatus of fluidized bed, spouted bed or the like in order to fluidize the water-soluble particles, and it is possible to use an apparatus such as a rotary pan and a tumbler in order to roll the water-soluble particles. By bringing the water-soluble particles into a flowing or rolling state, it becomes possible to form the coating layers continuously and it becomes possible to form the coating layers on the surface uniformly.

Additionally, the present invention may be performed in a facility for mass production. For example, it is possible to form the coating layers on 100 kg of the water-soluble particles as will be discussed in the Example. As a matter of course, the method of the present invention can be applied to the other than the facility for mass production.

A method for supplying a usable coating material such as the first and the second coating materials is required only to be one which can effectively achieve a dispersing addition. It is exemplified by spraying, dropping and the like. In particular, a method of a spraying addition with a two fluid nozzle using compressed air is able to form the coating layers excellently so as to be preferably utilized. Additionally, the coating materials may be independently supplied from one component to another. These may be mixed in an apparatus. Alternatively, it is also possible to supply these after previously mixing a part or the whole of the components.

The coating material is preferably supplied such that the mass of the coating layers per one layer is 0.5 to 5 mass %, more preferably 0.7 to 3 mass % relative to the mass of the coated water-soluble particles. A coating layer of lower than 0.5 mass % not only makes it difficult to form a uniform layer but also requires an increased number of lamination of the coating layers in order to obtain an aimed release property, which is therefore operationally inefficient. Meanwhile, a coating layer exceeding 5 mass % not only forms a thick and nonuniform layer but also abruptly increases the coating layer adhered to the interior of the apparatus, which sometimes results in reduction of use efficiency of the coating material. Particularly, a coating layer disposed on the outermost side (which may hereinafter be referred to as an outermost layer) may be thin unless a coating layer formed on the inner side of the outermost layer is seriously damaged, that is, it may be about 0.2 to 2 mass %.

A total quantity of the formed coating layers is preferably 1 to 15 mass % and more preferably 1.5 to 12 mass % relative to the mass of the coated water-soluble particles. With a total quantity of less than 1 mass %, it is difficult to attain an aimed release property. Meanwhile, a total quantity exceeding 15 mass % increases the thickness of the coating layers, so that water permeation and release of the water-soluble particles become difficult.

Moreover, the first coating material preferably contains an aromatic polyisocyanate, a polyol compound and an amine compound. The coating forms urethane resin. Additionally, the second coating material also preferably contains an aromatic polyisocyanate, a polyol compound and an amine compound. Furthermore, the coating material that contains the above components preferably has a low viscosity in order to coat the surfaces of the water-soluble particles with the coating material uniformly. For example, a viscosity of from 0.1 to 200 mPa·s is preferable in the coating temperature.

The above-mentioned aromatic polyisocyanate is exemplified by tolylene diisocyanate (TDI), methylenebis diisocyanate (MDI), naphthalene diisocyanate, polymethylene polyphenyl polyisocyanate, phenylene diisocyanate, xylylene diisocyanate, tetramethyl xylene diisocyanate, and modified substances of these such as a modified urea, a dimer, a trimer, a modified carbodiimide, a modified allophanate, a modified biuret and the like. These may be used in combination of two or more kinds, and may be the so-called crude polyisocyanate which is industrially usable. Among these, it is particularly preferable to use MDI, a crude MDI, a carbodiimidized MDI (liquid MDI), TDI, a crude TDI or the like.

Furthermore, the aromatic polyisocyanate may be used as a prepolymer that has an isocyanate end group and prepared from the aromatic polyisocyanatae. A method for preparing the prepolymer that has an isocyanate end group may be a publicly known one in which the prepolymer that has an isocyanate end group is obtained by reacting polyisocyanate with polyol at temperatures of from 30 to 130° C., preferably from 40 to 90° C. for 1 to 5 hours such that an equivalent ratio of isocyanate groups to active hydrogen groups is 1.1 to 50.0, preferably 1.2 to 25.0. By using the thus obtained MDI as the prepolymer that has an isocyanate end group, there are provided the effect of improving the compatibility with the other components, the effect of promoting the reaction, the effect of adjusting the viscosity to a workable level and the like.

The above-mentioned polyol component is exemplified by castor oil and a castor oil derivative (i.e. castor oil, an adduct between castor oil and alkylene oxide, a castor oil fatty acid modified by polyalcohol and the like), an adduct between a low molecular-weight polyfunctional alcohol and alkylene oxide (i.e., a single adduct or a coadduct between diols, triols, hexaols, glycerin or trimethylolpropane and propylene oxide, butylene oxide or styrene oxide), an adduct between a low molecular-weight polyfunctional carboxylic acid and alkylene oxide (i.e., a single adduct or a coadduct between dodecanedioic acid and propylene oxide, butylene oxide or styrene oxide), an adduct between a low molecular-weight polyfunctional polyester and alkylene oxide (i.e., a single adduct or a coadduct between polyester of glycerin and dodecanedioic acid, and propylene oxide, butylene oxide or styrene oxide), and a mixture of two or more kinds of these. Among these, there may be preferably used: a castor oil; a castor oil derivative prepared by ester interchange reactions with ethylene glycol or propylene glycol; polyoxyethylene triol; and polyoxypropylene triol.

As the above-mentioned amine compound, alkylamine or an amine-based polyol is used. Alkylamine is exemplified by trimethylamine, triethylamine, dimethylethylamine and dimethylisopropylamine. It is preferable to use the amine-based polyol as the amine compound, the amine-based polyol being exemplified by: a low-molecular-weight amine-based polyol (such as diethanol amine, triethanol amine, and N-methyl-N, N'-diethanol amine); and an amine-based polyol obtained by an addition reaction of an amino compound such as ethylenediamine, 1,3-propanediamine and 1,6-hexanediamine with an alkylene oxide (e.g., propylene oxide (PO) and ethylene oxide (EO)). An addition ratio is not particularly limited but it is preferable that the number of the alkylene oxide is 1 to 200, preferably 1 to 50, per one nitrogen atom. This number is particularly preferably from about 2 to 2.4 in order to adjust properties regarding hydrophilicity of the coating layers. Examples thereof include N,N,N',N'-tetrakis[2-hydroxypropyl]ethylenediamine, N,N,N',N'-tetrakis[2-hydroxyethyl] ethylenediamine, N,N,N',N'-tetrakis[2-hydroxypropyl]-1,3-propane diamine, N,N,N',N'-tetrakis[2-hydroxyethyl]-1,6-hexanediamine, and the like. In view of improving the reactivity and property, the particularly preferable examples include N,N,N',N'-tetrakis[2-hydroxypropyl]ethylenediamine, N,N,N',N'-tetrakis[2-hydroxyethyl]ethylenediamine, and oxypropylethylenediamine or oxyethylethylenediamine having these as a primary component.

In view of providing a good compatibility with the other components and in view of readily forming uniform coating layers, it is preferable to use the amine-based polyol as the above-mentioned polyol component. The amine-based polyol is preferable because it promotes the reaction and functions as a cross-linking agent and a chain elongation agent to provide an excellent curing property and tough coating layers. Furthermore, the amount of the amine-based polyol to be used is required only to be adjusted such that the cross-linking reaction begins after the coating layers are uniformly formed.

In the coating material such as the first and the second coating materials, isocyanate groups and hydroxyl groups in the total of the isocyanate component and the polyol component preferably has a mole ratio of isocyanate groups/hydroxyl groups of 0.6 to 1.5. When the ratio is lower than 0.6 or higher than 1.5, cross-linking in the obtained coating layers is so insufficient that the release rate of the component of the water-soluble particles may not reach a preferable one. Additionally, for the purpose of imparting flexibility to the coating layers while not allowing the coating layers to have unreacted isocianate groups, it is preferable to provide a ratio of isocyanate groups/hydroxyl groups of 0.6 to 0.99. It is further preferable to prepare the outermost layers at a ratio of isocyanate groups/hydroxyl groups of 1 to 1.5 when coating layers disposed on the inner side of the outermost layers are provided at a ratio of isocyanate groups/hydroxyl groups of 0.6 to 0.99 as discussed above, since excessive hydroxyl groups on the surfaces of the coating layers can be reacted with excessive isocyanate groups in the outermost layers to allow more effective formation of the coating layers.

After formation of the coating layers, the coating bodies are subjected to heating in a flowing or rolling state to cure the coating layers, thereby providing the coated water-soluble particles. A heat time therefor depends on the heat temperature and the kind and amount of the coating material. However, it is required only to perform heating until at least the outermost layers become free from the adhesion property. In order to promote the urethane reaction, heating may be performed further after the outermost layers become free from the adhesion property; however, an excessively long period of heating time not only reduces the productivity but also wears the outermost layers due to contact with the coating apparatus to inflict an injury on the surfaces of the outermost layers. Therefore, heating is required to be performed to such an extent as not to inflict an injury. For example, the heating time may be shorter than ten times a time at which the outermost layers become free from the adhesion property. The method for heating preferably includes using heat conducted from the apparatus, hot wind or the like.

To the first and the second coating materials, a catalyst may be added in order to accelerate the formation of urethane bond. For example, an organic metal catalyst e.g. dibutyltin dilaurate and lead octenate may be used.

Additionally, it is optional for the coating material to contain a super absorbent polymer, a vegetable oil or the like for the purpose of regulating the release property and adhesion property of the coating layers obtained from the coating material such as the first and the second coating materials.

The vegetable oil is an unreacted component, and is able to make a three-dimensional structure of urethane bond loose when serving as cavities. With this, water permeation through the cavities becomes easily achieved to diminish the adhesion property during thermosetting of the coating material. Though there is no problem even in a single addition of the vegetable oil, it is preferable that the vegetable oil is previously mixed with the isocyanate component, the polyol component or the like thereby to be supplied in the form of a uniform liquid.

The vegetable oil is exemplified by coconut oil, corn oil, cottonseed oil, olive oil, palm oil, peanut oil, rapeseed oil, canola oil, safflower oil, sesame oil, soybean oil, sunflower seed oil, linseed oil, tall oil, and a mixture of these. Among these, a vegetable oil highly containing an oleic or linoleic acid component is preferably employed; more preferably it is rapeseed oil, canola oil, soybean oil or the like, and much more preferably rapeseed oil or canola oil. furthermore, a part or the entire of the vegetable oil may be substituted with triglyceride of fatty acid contained in these vegetable oils. The fatty acid is exemplified by capric acid, lauric acid, myristic acid, palmitic acid, stearic acid, arachidic acid, behenic acid, oleic acid, erucic acid, linoleic acid, linolenic acid, ricinoleic acid and the like.

The super absorbent polymer is a substance that absorbs a large quantity of water thereby swelling to have a volume at least five times its dry volume. In particular, it is preferable to use one that exhibits low solubility and becomes a gel when the substance has absorbed water. For example, it is possible to cite: an acrylate polymer (i.e. SUMIKAGEL S, L and R types available from SUMITOMO CHEMICAL CO., LTD., AQUAKEEP 10SH, 10SHP, 10SH-NF(20), SA60NTYPE2 available from Sumitomo Seika Chemicals Co., Ltd., AQUA-MATE AQ-200 and AQ-200B-02 available from Sekisui Plastics Co., LTD., and SUNFRESH ST-250 MPS and ST-500 MPSA available from SANYO CHEMICAL INDUSTRIES, LTD.); an isobutylene polymer (i.e. KI GEL-201K, KI GEL-201K-F2, KI GEL SOLUTION SYSTEM and KI GEL COMPOUND available from KURARAY CO., LTD.); an acrylate-vinyl alcohol copolymer; a resin modified with a polyethylene oxide; a starch graft polymer; starch (such as potato starch, corn starch, sweet potato starch, and soluble starch); carboxymethyl cellulose (CMC); a metal salt of CMC; and bentonite. Of these, it is preferable to use the acrylate polymer, the isobutylene polymer or starch, and particularly preferably the acrylate polymer.

The super absorbent polymer preferably has a particle diameter of from 1 to 100 μm, more preferably from 2 to 50 μm. If it is less than 1 μm, there is a little change in the release timing and the release rate even with the addition of the super absorbent polymer. Meanwhile, if it is more than 100 μm, the coating layers cannot obtain a good uniformity and therefore tend to have defects on their surfaces.

The added amount of the super absorbent polymer is to be changed depending on the particle diameter, and it is normally from 0.1 to 30 mass %, preferably from 0.5 to 20 mass %, more preferably from 1 to 10 mass % relative to the total mass of the urethane resin and the super absorbent polymer. If it is less than 0.1 mass %, there is a little change in the release timing and the release rate even with the addition of the super absorbent polymer; therefore, it is not effective to regulating the release property with the super absorbent polymer of less than 0.1 mass %. Meanwhile, if it exceeds 30 mass %, it may become difficult to regulate the timing of stating the release, due to increase of hydrophilicity.

The super absorbent polymer is previously mixed with the polyol component to disperse therein thereby preparing a dispersion. The dispersion is added to the polyisocyanate component, and immediately after this, added to the water-soluble particles, thereby preferably supplying the super absorbent polymer. Alternatively these components may be independently added to the water-soluble particles in the coating apparatus. Furthermore, the super absorbent polymer may be disposed in any layer unless the layers containing the super absorbent polymer are the outermost layers.

Additionally, it is possible to add an organic or inorganic additive other than the super absorbent polymer to the coating material such as the first and the second coating materials unless the properties of the coating layers of the present invention are not substantially impaired. The additive can be exemplified by alkyd resin, urethane resin, fatty acid ester, rosin and its derivatives, ester gum, surfactant, petroleum resin, talc, diatomaceous earth, silica, urea, sulfur powder and the like. These may be added in an amount of from 0.1 to 50 parts by mass relative to 100 parts by mass of the urethane resin of the present invention. Moreover, it is also possible to regulate the workability and the release property by the kind or the addition amount of these.

Furthermore, the surfaces of the coated water-soluble particles of the present invention may be treated with an inorganic powder for the purpose of preventing the coated water-soluble particles from adhering to each other. The inorganic powder is exemplified by talc, sulfur, calcium carbonate, silica, zeolite, diatomaceous earth, clay, metal oxides and the like. These may be used singly or in combination. In view of easiness in handling, talc is preferably used.

The inorganic powder is preferably used in an amount of 0.1 to 15 mass %, more preferably 1 to 10 mass % relative to the coating layers. If it is less than 0.1 mass %, the effect of preventing adhesion is little. Meanwhile, even if used in an amount exceeding 15 mass %, the inorganic powder does not adhere to the surfaces of the coated water-soluble particles. Additionally, the inorganic powder is sprayed onto the coated water-soluble particles which are in a flowing or rolling state, after forming the outermost layers, which is preferable since the inorganic powder remains on the surfaces of the outermost layers and never be embedded in the coating layers so as to make the release stable.

The coated water-soluble particles of the present invention are preferably used as a coated particulate fertilizer formed by coating a particulate fertilizer, since a release pattern for a released component is adjustable. The coated particulate fertilizer is required only to be a water-soluble particulate fertilizer and is exemplified by a fertilizer or a complex fertilizer formed of at least one kind selected from the group consisting of urea, ammonium chloride, ammonium sulfate, ammonium nitrate, potassium chloride, potassium sulfate, potassium nitrate, sodium nitrate, potassium phosphate, ammonium phosphate and calcium phosphate a particulate organic fertilizers and the like.

Additionally, the coated water-soluble particles of the present invention are preferably used as a coated particulate agricultural chemical formed by coating a particulate agricultural chemical. The coated particulate agricultural chemical is required only to be a water-soluble particulate agricultural chemical and is exemplified by various kinds of insecticides, insect repellents, antiseptics, herbicides, rodenticides, plant growth regulators and the like.

EXAMPLES

The present invention will be discussed with reference to the following Examples; however, the present invention is not limited by these Examples. Moreover, the production condition for the present invention is shown in Table 1.

Example 1

A drum-type rolling coating apparatus having a diameter of 1.4 m was charged with 100 kg of urea particles (having a particle diameter of from 2.5 to 4.0 mm). Then, the urea particles were rolled at 7 rpm while being kept at 70° C. by using a hot wind generator In order to form first coating layers, there was prepared a coating material containing: 764 g of a mixture liquid prepared by mixing a castor oil (having a hydroxyl value of 160 mg KOH/g) and an adduct between ethylenediamine and propylene oxide (having a propylene oxide/nitrogen atom ratio of 2.2 and a hydroxyl value of 760 mg KOH/g) such that a mole ratio of hydroxyl groups therebetween resulted in 8:2; and 839 g of a MDI-modified castor oil (i.e., a prepolymer that has an isocyanate end group, prepared by mixing a castor oil with an excessive amount of MDI to adjust the mass of isocyanate groups to 19 mass % relative to the total mass). The coating material (1,603 g in total, which corresponded to an amount of 1.6 mass % and a thickness of 10.8 µm) was sprayed (or applied) into the apparatus for 30 seconds with using a two fluid nozzle, thereby forming coating bodies. The coating bodies began adhering with an elapse of 2.5 minutes after the spraying of the coating material, and the apparent volume reached maximum with an elapse of 3 minutes. Furthermore, it was confirmed that the coating bodies were strongly adhered to each other but aggregated particles were partly broken with an elapse of 3.5 minutes.

Then, with an elapse of 3.5 minutes after the spraying of the coating material for the first layers, a coating material having the same composition and the same amount (1.6 mass %) as the first layers was sprayed into the apparatus for 30 seconds with using a two fluid nozzle, in order to form second coating layers.

Subsequently, with an elapse of 3.5 minutes after finishing the spraying of the coating material for the second layers, a coating material having the same composition as the first layers (534 g in total, which corresponded to an amount of 0.5 mass % and a thickness of 3.6 µm) was sprayed into the apparatus for 10 seconds with using a two fluid nozzle, thereby forming outermost layers. It was confirmed that: the coating bodies began adhering with an elapse of about 2.5 minutes after the spraying of the coating material for the outermost layers; the aggregated particles were not yet formed with an elapse of 3.0 minutes though the coating bodies were strongly adhered to each other; the volume of the aggregated particles began to decrease with an elapse of 3.5 minutes; and the coating bodies which were in a condition of adhering became extinct with an elapse of 7 minutes.

The coating bodies were rolled for 30 minutes from the completion of the spraying of the coating material for the outermost layers to cure the coating layers. It was then cooled down to the ordinary temperature (about 25° C.) thereby obtaining aimed coated fertilizer particles.

The obtained coated fertilizer particles were measured in terms of a non-defective ratio and a coated ratio, the results of which were indicated in Table 2. It was found from Table 2 that a reduction in the non-defective ratio (that should have proceeded together with the lapse of time) was suppressed, and additionally defects on the coating layers were extensively restrained. At this time, the coated ratio was 3.5 mass % and the thickness of the coating layers was 25 µm.

TABLE 1

| | Coated ratio (mass %) | | Coating interval (min) | Coating material | | | |
|---|---|---|---|---|---|---|---|
| | The whole | layer composition | | Isocyanate component | Polyol component | Amine compound | Other |
| Example 1 | 3.5 | 1.5 + 1.5 + 0.5 | 3.5 | MDI-modified castor oil | Castor oil | Adduct between ethylenediamine and propylene oxide | — |
| Example 2 | 4 | 1.5 + 1.5 + 1.0 | 3.5 | MDI-modified castor oil | Castor oil | Adduct between ethylenediamine and propylene oxide | — |
| Example 3 | 3.2 | 1.5 + 1.5 + 0.2 | 3.5 | MDI-modified castor oil | Castor oil | Adduct between ethylenediamine and propylene oxide | — |
| Example 4 | 3.5 | 1.5 + 1.5 + 0.5 | 2.8 | MDI-modified castor oil | Castor oil | Adduct between ethylenediamine and propylene oxide | — |
| Example 5 | 4.5 | 1.5 + 2.5 + 0.5 | 1.5, 1.8 | MDI oligomer | Castor oil | Adduct between ethylenediamine and propylene oxide | — |
| Example 6 | 4.5 | 1.3 + 1.3 + 1.3 + 0.5 | 4.5 | MDI-modified castor oil | Polypropylene triol | Adduct between ethylenediamine and propylene oxide | — |
| Example 7 | 8 | 1.5 + 1.5 + 2.0 + 2.0 + 1.0 | 3.5, 4 | MDI-modified castor oil | Castor oil | Adduct between ethylenediamine and propylene oxide | Super absorbent polymer |
| Comparative Example 1 | 3 | 1.5 + 1.5 | 10 | MDI-modified castor oil | Castor oil | Adduct between ethylenediamine and propylene oxide | — |
| Comparative Example 2 | 3.5 | 1.75 + 1.75 | 10 | MDI-modified castor oil | Castor oil | Adduct between ethylenediamine and propylene oxide | — |
| Comparative Example 3 | 8 | 1.5 + 1.5 + 2.0 + 2.0 + 1.0 | 10 | MDI-modified castor oil | Castor oil | Adduct between ethylenediamine and propylene oxide | Super absorbent polymer |
| Comparative Example 4 | 3.5 | 0.5 + 0.5 + 0.5 + 0.5 + 0.5 + 0.5 + 0.5 | 7 | MDI-modified castor oil | Castor oil | Adduct between ethylenediamine and propylene oxide | — |
| Comparative Example 5 | 3.5 | 1.5 + 1.5 + 0.5 | 10 | MDI-modified castor oil | Castor oil | Adduct between ethylenediamine and propylene oxide | — |
| Comparative Example 6 | 3.5 | 1.5 + 1.5 + 0.5 | 2 | MDI-modified castor oil | Castor oil | Adduct between ethylenediamine and propylene oxide | — |

[Evaluation of Non-Defective Ratio]

The coated fertilizer particles were taken out after an elapse of a certain period of time and measured in respect to the non-defective ratio, in order to confirm defects caused within 30 minutes of heating performed after spraying the coating material for the outermost layers.

The coated fertilizer particles having been subjected to reduction was taken out in an amount of 10 g, and a diluents (2.5 g/250 ml pure water) formed by previously diluting an ink (S-1 (red) available from Shachihata Inc.) was added thereto. It was allowed to stand still at 25° C. for 1 hour, and then filtration was conducted to recover the coated fertilizer particles. Subsequently, the ink adhered to the coated fertilizer particles was rinsed with water. The coated fertilizer particles colored with the ink, and the coating layers that accomplished the release were removed to obtain the mass of an uncolored coated fertilizer particles, from which the non-defective ratio was calculated ((the mass of the uncolored coated fertilizer particles) g/10 g×100). The results are shown in Table 2.

[Measurement of Coated Ratio]

Upon subjecting the obtained coated fertilizer particles to reduction, the coated ratio was calculated ((the mass of the coating layer/the mass of the coated fertilizer particles)×100).

TABLE 2

| | Coated ratio (mass %) | | | Non-detective ratio (%) | | | |
|---|---|---|---|---|---|---|---|
| | The whole | layer composition | Temperature (° C.) | 3.5 min later | 7 min later | 20 min later | 30 min later |
| Example 1 | 3.5 | 1.5 + 1.5 + 0.5 | 70 | 88 | 86 | 84 | 84 |
| Example 2 | 4 | 1.5 + 1.5 + 1.0 | 70 | 95 | 95 | 93 | 93 |
| Example 3 | 3.2 | 1.5 + 1.5 + 0.2 | 70 | 84 | 77 | 72 | 71 |
| Example 4 | 3.5 | 1.5 + 1.5 + 0.5 | 70 | 91 | 88 | 84 | 83 |
| Example 5 | 4.5 | 1.5 + 2.5 + 0.5 | 60 | 98 | 98 | 98 | — |
| Example 6 | 4.5 | 1.3 + 1.3 + 1.3 + 0.5 | 70 | 96 | 95 | 94 | 93 |
| Example 7 | 8 | 1.5 + 1.5 + 2.0 + 2.0 + 1.0 | 70 | 100 | 100 | 100 | 100 |

TABLE 2-continued

| | Coated ratio (mass %) | | | Non-detective ratio (%) | | | |
|---|---|---|---|---|---|---|---|
| | The whole | layer composition | Temperature (° C.) | 3.5 min later | 7 min later | 20 min later | 30 min later |
| Comparative Example 1 | 3 | 1.5 + 1.5 | 70 | 64 | 38 | 25 | 23 |
| Comparative Example 2 | 3.5 | 1.75 + 1.75 | 70 | 83 | 64 | 57 | 55 |
| Comparative Example 3 | 8 | 1.5 + 1.5 + 2.0 + 2.0 + 1.0 | 70 | 99 | 98 | 98 | 97 |
| Comparative Example 4 | 3.5 | 0.5 + 0.5 + 0.5 + 0.5 + 0.5 + 0.5 | 70 | 80 | 73 | 72 | 72 |
| Comparative Example 5 | 3.5 | 1.5 + 1.5 + 0.5 | 70 | 81 | 68 | 63 | 60 |
| Comparative Example 6 | 3.5 | 1.5 + 1.5 + 0.5 | 70 | 86 | 80 | 77 | 74 |

Example 2

A procedure of Example 1 was repeated with the exception that the mass of the coating material sprayed as the outermost layers was changed to 1,074 g in total (which corresponded to an amount of 1.0 mass % and a thickness of 7.2 μm) thereby obtaining the coated fertilizer particles. On the obtained coated fertilizer particles, an evaluation of the non-defective ratio and a measurement of the coated ratio were performed. It was found from Table 2 that a reduction in the non-defective ratio (that should have proceeded together with the lapse of time) was suppressed, and additionally defects on the coating layers were extensively restrained. At this time, the coated ratio was 4.0 mass % and the thickness of the coating layers was 29 μm.

Example 3

A procedure of Example 1 was repeated with the exception that the mass of the coating material sprayed as the outermost layers was changed to 213 g in total (which corresponded to an amount of 0.2 mass % and a thickness of 1.4 μm) thereby obtaining the coated fertilizer particles. On the obtained coated fertilizer particles, an evaluation of the non-defective ratio and a measurement of the coated ratio were performed. It was found from Table 2 that a reduction in the non-defective ratio (that should have proceeded together with the lapse of time) was suppressed, and additionally defects on the coating layers were extensively restrained. At this time, the coated ratio was 3.2 mass % and the thickness of the coating layers was 23 μm.

Example 4

A procedure of Example 1 was repeated with the exception that the spraying of the coating material for the second layers was started with an elapse of 2.8 minutes after the spraying of the coating material for the first layers (immediately before the volume of the aggregated particles reached maximum) and that the spraying of the coating material for the outermost layers was started with an elapse of 2.8 minutes after finishing the spraying of the coating material for the second layers, thereby obtaining the coated fertilizer particles. On the obtained coated fertilizer particles, an evaluation of the non-defective ratio and a measurement of the coated ratio were performed. It was found from Table 2 to be possible to extensively restrain defects of the coating layers, similarly to Example 1. At this time, the coated ratio was 3.5 mass % and the thickness of the coating layers was 25 μm.

Example 5

A procedure of Example 1 was repeated with the exception of the following, thereby obtaining the coated fertilizer particles:

The urea particles were kept at a temperature of 60° C. In forming first coating layers, there was prepared a coating material containing: 967 g of a mixture liquid prepared by mixing a castor oil and an adduct between ethylenediamine and propylene oxide such that a mole ratio of hydroxyl groups therebetween resulted in 8:2; and 653 g of a MDI oligomer (having an average molecular weight of about 400). The coating material (1,620 g in total, which corresponded to an amount of 1.6 mass % and a thickness of 11.0 μm) was sprayed into the apparatus for 30 seconds with using a two fluid nozzle. With an elapse of 1.5 minutes after the spraying of the coating material for the first layers, a coating material (2,700 g in total, which corresponded to an amount of 2.6 mass % and a thickness of 18.3 μm) having the same composition as the first layers was sprayed into the apparatus for 30 seconds with using a two fluid nozzle, thereby forming second layers. Furthermore, a coating material (540 g in total, which corresponded to an amount of 0.5 mass % and a thickness of 3.7 μm) having the same composition as the first layers was sprayed into the apparatus for 10 seconds with using a two fluid nozzle, with an elapse of 1.8 minutes after the spraying of the coating material for the second layers, thereby forming outermost layers. Then, 20 minutes of rolling was conducted to cure the coating layers of the coating bodies, thereby obtaining the coated fertilizer particles. On the obtained coated fertilizer particles, an evaluation of the non-defective ratio and a measurement of the coated ratio were performed.

Aside from the above, the coating material of Example 5 previously received an investigation as follows. In the coating material for the first layers, the coating bodies began adhering with an elapse of 1 minute after the spraying, and the aggregated particles reached maximum with an elapse of 1.5 minutes. With an elapse of 2 minutes, the coating bodies were strongly adhered to each other but the aggregated particles were brought into a condition of being broken. Meanwhile, in the coating material for the second layers, the coating bodies began adhering with an elapse of 1.5 minutes after the spraying, and the aggregated particles reached maximum with an elapse of 2 minutes. With an elapse of 3 minutes, the coating bodies were strongly adhered to each other but the aggregated particles were brought into a condition of being broken. Furthermore, in the coating material for the outermost layers, the coating bodies which were in a condition of adhering became extinct with an elapse of 5 minutes after the spraying.

It was found from Table 2 that a reduction in the non-defective ratio (that should have proceeded together with the lapse of time) was suppressed, and additionally defects on the coating layers were extensively restrained. At this time, the coated ratio was 4.5 mass % and the thickness of the coating layers was 33 μm.

Example 6

A procedure of Example 1 was repeated with the exception of the following, thereby obtaining the coated fertilizer particles:

In forming first coating layers, there was prepared a coating material (1,440 g in total, which corresponded to an amount of 1.4 mass % and a thickness of 9.5 μm) containing: 562 g of a mixture liquid prepared by mixing polypropylene triol (having a hydroxyl value of 280 mg KOH/g) and an adduct between ethylenediamine and propylene oxide such that a mole ratio of hydroxyl groups therebetween resulted in 75:25; and 878 g of a MDI-modified castor oil. With an elapse of 4.5 minutes after the spraying of the coating material for the first layers, spraying of the second layers was started in such a manner as to spray a coating material having the same composition as the first layers into the apparatus for 30 seconds with using a two fluid nozzle. Spraying third layers was started with an elapse of 4.5 minutes after finishing the spraying of the second layers. Furthermore, a coating material (540 g in total, which corresponded to an amount of 0.5 mass % and a thickness of 0.5 μm) having the same composition as the first layers was sprayed into the apparatus for 10 seconds with using a two fluid nozzle, with an elapse of 4.5 minutes after the spraying of the third layers to form outermost layers. On the obtained coated fertilizer particles, an evaluation of the non-defective ratio and a measurement of the coated ratio were performed.

Aside from the above, the coating material of Example 6 previously received an investigation as follows. In the coating material for the first to third layers, the coating bodies began adhering with an elapse of 3.5 minutes after the spraying, and the aggregated particles stared to be formed with an elapse of 4 minutes. With an elapse of 4.5 minutes, the coating bodies were strongly adhered to each other but the aggregated particles were brought into a condition of being broken. Furthermore, in the coating material for the outermost layers, the coating bodies which were in a condition of adhering became extinct with an elapse of 10 minutes after finishing the spraying.

It was found from Table 2 that a reduction in the non-defective ratio (that should have proceeded together with the lapse of time) was suppressed, and additionally defects on the coating layers were extensively restrained. At this time, the coated ratio was 4.5 mass % and the thickness of the coating layers was 33 μm.

Example 7

A drum-type rolling coating apparatus having a diameter of 1.4 m was charged with 100 kg of urea particles (having a particle diameter of from 2.5 to 4.0 mm). Then, the urea particles were rolled at 7 rpm while being kept at 70° C. by using a hot wind generator.

In order to form first coating layers, there was prepared a coating material containing: 772 g of a mixture liquid prepared by mixing a castor oil (having a hydroxyl value of 160 mg KOH/g) and an adduct between ethylenediamine and propylene oxide (having a propylene oxide/nitrogen atom ratio of 2.2 and a hydroxyl value of 760 mg KOH/g) such that a mole ratio of hydroxyl groups therebetween resulted in 8:2; 64 g of a super absorbent polymer (a cross-linked acrylate polymer having an average particle diameter of 25 μm; ST-500 MPSA available from SANYO CHEMICAL INDUSTRIES, LTD.); and 848 g of a MDI-modified castor oil (i.e., a prepolymer that has an isocyanate end group, prepared by mixing a castor oil with an excessive amount of MDI to adjust the mass of isocyanate groups to 19 mass % relative to the total mass). The coating material (1,684 g in total, which corresponded to an amount of 1.7 mass % and a thickness of 11.4 μm) was sprayed (or applied) into the apparatus for 30 seconds with using a two fluid nozzle. With an elapse of 3.5 minutes after the spraying for forming the first layers, a coating material having the same composition and the same amount as the first layers was sprayed into the apparatus for 30 seconds with using a two fluid nozzle, thereby forming second coating layers.

Subsequently, with an elapse of 3.5 minutes after the spraying for forming the second layers, there was prepared a coating material containing: 1,070 g of a mixture liquid prepared by mixing a castor oil (having a hydroxyl value of 160 mg KOH/g) and an adduct between ethylenediamine and propylene oxide (having a propylene oxide/nitrogen atom ratio of 2.2 and a hydroxyl value of 760 mg KOH/g) such that a mole ratio of hydroxyl groups therebetween resulted in 8:2; and 1,175 g of a MDI-modified castor oil (i.e., a prepolymer that has an isocyanate end group, prepared by mixing a castor oil with an excessive amount of MDI to adjust the mass of isocyanate groups to 19 mass % relative to the total mass). The coating material (2,245 g in total, which corresponded to an amount of 2.1 mass % and a thickness of 15.3 μm) was sprayed (or applied) into the apparatus for 30 seconds with using a two fluid nozzle, thereby forming third coating layers. With an elapse of 4 minutes after the spraying for forming the third layers, a coating material having the same composition and the same amount as the third layers was sprayed (or applied) into the apparatus for 30 seconds with using a two fluid nozzle, thereby forming fourth coating layers.

With an elapse of 4 minutes after the spraying for forming the fourth layers, a coating material (1,122 g in total, which corresponded to an amount of 1.0 mass % and a thickness of 3.8 μm) having the same composition as the third layers was sprayed (or applied) into the apparatus for 10 seconds with using a two fluid nozzle, thereby forming outermost layers. In forming the outermost layers, the coating bodies which were in a condition of adhering became extinct with an elapse of 7 minutes after finishing the spraying.

Then, rolling was started after finishing the spraying for forming the outermost layers and continued for 30 minutes, thereby forming coating layers on the coating bodies. It was then cooled down to the ordinary temperature (about 25° C.) thereby obtaining aimed coated fertilizer particles. On the obtained coated fertilizer particles, an evaluation of the non-defective ratio and a measurement of the coated ratio were performed. It was found from Table 2 that a reduction in the non-defective ratio (that should have proceeded together with the lapse of time) was suppressed, and additionally defects on the coating layers were extensively restrained. At this time, the coated ratio was 8 mass % and the thickness of the coating layers was 60 μm. Additionally, a thermosetting reaction caused in the coating material of Example 7 indicated the same trend as the coating material of Example 1.

Comparative Example 1

A procedure of Example 1 was repeated with the exception that an interval between spraying the coating material for the first layers and spraying the coating material for the second layers was set at 10 minutes and that the third layers were not formed, thereby obtaining the coated fertilizer particles. On the obtained coated fertilizer particles, an evaluation of the non-defective ratio and a measurement of the coated ratio were performed. It was found from Table 2 that the non-defective ratio is largely reduced with the lapse of time, and additionally defects on the coating layers were increased. At this time, the coated ratio was 3.0 mass % and the thickness of the coating layers was 22 µm.

Comparative Example 2

A procedure of Example 1 was repeated with the exception that: the coating material for forming the first and the second layers was sprayed in an amount of 1,870 g (which corresponded to an amount of 1.75 mass % and a thickness of 12.5 µm); an interval between spraying the coating materials was set at 10 minutes; and the third layers were not formed, thereby obtaining the coated fertilizer particles. On the obtained coated fertilizer particles, an evaluation of the non-defective ratio and a measurement of the coated ratio were performed. It was found from Table 2 that the non-defective ratio is largely reduced with the lapse of time, and additionally defects on the coating layers were increased. At this time, the coated ratio was 3.5 mass % and the thickness of the coating layers was 25 µm.

Comparative Example 3

A procedure of Example 7 was repeated with the exception that an interval between spraying the coating materials was set at 10 minutes, thereby obtaining the coated fertilizer particles. On the obtained coated fertilizer particles, an evaluation of the non-defective ratio and a measurement of the coated ratio were performed. It was found from Table 2 that the non-defective ratio is reduced with the lapse of time, and additionally defects were caused on the coating layers. At this time, the coated ratio was 8 mass % and the thickness of the coating layers was 60 µm.

Comparative Example 4

A procedure of Example 1 was repeated with the exception that: the number of the coating layers was changed to seven layers; the coating material was sprayed in an amount of 508 g (which corresponded to an amount of 0.5 mass % and a thickness of 3.5 µm); the interval for spraying the coating materials was changed to 7 minutes; and all of the seven coating layers were sprayed in the same amount, thereby obtaining the coated fertilizer particles. On the obtained coated fertilizer particles, an evaluation of the non-defective ratio and a measurement of the coated ratio were performed. It was found from Table 2 that the non-defective ratio is largely reduced with the lapse of time, and additionally defects on the coating layers were increased. At this time, the coated ratio was 3.5 mass % and the thickness of the coating layers was 25 µm.

Comparative Example 5

A procedure of Example 1 was repeated with the exception that the interval for spraying the coating materials was changed to 10 minutes, thereby obtaining the coated fertilizer particles. On the obtained coated fertilizer particles, an evaluation of the non-defective ratio and a measurement of the coated ratio were performed. It was found from Table 2 that the non-defective ratio is largely reduced with the lapse of time, and additionally defects on the coating layers were increased. At this time, the coated ratio was 3.5 mass % and the thickness of the coating layers was 25 µm.

Comparative Example 6

A procedure of Example 1 was repeated with the exception that the interval for spraying the coating materials was changed to 2 minutes, thereby obtaining the coated fertilizer particles. On the obtained coated fertilizer particles, an evaluation of the non-defective ratio and a measurement of the coated ratio were performed. It was found from Table 2 that the non-defective ratio is largely reduced with the lapse of time, and additionally defects on the coating layers were increased. At this time, the coated ratio was 3.2 mass % and the thickness of the coating layers was 23 µm. Additionally a good coating was not formed.

As a result of making a comparison among the examples having an entire coated ratio of 3.5 mass %, i.e., Examples 1 and 4 and Comparative Examples 2 and 4 to 6, it was found that Examples 1 and 4 were superior to Comparative Example 2 having a smaller number of the coating layers, in respect of the non-defective ratio. Additionally, Examples 1 and 4 were superior to Comparative Examples 4 to 6 having the same number of the coating layers, in respect of the non-defective ratio.

Furthermore, it was found from a comparison between Examples 1 and 4 that their non-defective ratios were almost equal. From this, it was proved that a good non-defective ratio was maintained in forming coating films, even if the next coating material was sprayed under a condition where curing of the thermosetting resin that was to form the coating layers was not sufficient. Additionally, a comparison among Examples 1 and 4 and Comparative Examples 5 and 6 proved that the non-defective ratio was largely reduced by sufficiently curing the coating layers and then forming the next layers. Meanwhile, it was found that the non-defective ratio was reduced also in a case where the spraying of the coating material was too early.

Moreover, by making a comparison between the examples having an entire coated ratio of 8 mass %, i.e., Example 7 and Comparative Example 3, it was found that both of them accomplished high non-defective ratios. This proved that the non-defective ratio could be improved by increasing the coated ratio. Additionally, Comparative Example 4 also can be said to be able to accomplish a greater non-defective ratio because of a coated ratio of 3.5 mass % and its multilayered structure; however, Comparative Examples 3 and 4 (where each of the laminated coating layers was subjected to thermosetting sufficiently one by one) required a long period of production time and therefore not suitable for the object of the present invention.

In view of the above, it was proved that the coated fertilizer particles could be obtained with excellent non-defective ratios even when the entire coated ratio was the same, by laminating the next layer in a condition where a thermosetting resin which formed the coating layer caused thermosetting insufficiently. It was also proved that the production time could be shortened thereby.

[Release Test]

Examples 1 to 7 and Comparative Example 1 to 6 were subjected to a release test by carrying out reduction on the obtained coated fertilizer particles. The results thereof are shown in Table 3. In the release test, the coated fertilizer particles having been subjected to reduction was taken out in an amount of 10 g, added to 200 cc of ion exchange water and kept in a thermostat of 25° C. After an elapse of a certain period of time, it was taken out and then the amount of released urea in water was determined. Incidentally, Table 3 shows the number of days that had been taken to confirm a released urea of 10%, 50% and 80%.

TABLE 3

| | Coated ratio (mass %) | | Number of days taken until release (day) | | |
|---|---|---|---|---|---|
| | The whole | layer composition | 10% | 50% | 80% |
| Example 1 | 3.5 | 1.5 + 1.5 + 0.5 | 8 | 43 | 70 |
| Example 2 | 4 | 1.5 + 1.5 + 1.0 | 22 | 50 | 77 |
| Example 3 | 3.2 | 1.5 + 1.5 + 0.2 | 2 | 26 | 48 |
| Example 4 | 3.5 | 1.5 + 1.5 + 0.5 | 3 | 40 | 64 |
| Example 5 | 4.5 | 1.5 + 2.5 + 0.5 | 22 | 41 | 69 |
| Example 6 | 4.5 | 1.3 + 1.3 + 1.3 + 0.5 | 25 | 59 | 94 |
| Example 7 | 8 | 1.5 + 1.5 + 2.0 + 2.0 + 1.0 | 109 | 142 | 168 |
| Comparative Example 1 | 3 | 1.5 + 1.5 | 1 | 3 | 27 |
| Comparative Example 2 | 3.5 | 1.75 + 1.75 | 1 | 22 | 52 |
| Comparative Example 3 | 8 | 1.5 + 1.5 + 2.0 + 2.0 + 1.0 | 69 | 106 | 127 |
| Comparative Example 4 | 3.5 | 0.5 + 0.5 + 0.5 + 0.5 + 0.5 + 0.5 + 0.5 | 2 | 27 | 51 |
| Comparative Example 5 | 3.5 | 1.5 + 1.5 + 0.5 | 1 | 23 | 52 |
| Comparative Example 6 | 3.5 | 1.5 + 1.5 + 0.5 | 1 | 26 | 56 |

It was found from Table 3 that Examples 1, 4 and 7 could keep the effect of controlling the release longer than Comparative Examples 2 to 6 could do even if the coated ratios were the same, and that the effect of controlling the release was great particularly at an early stage. Furthermore, by making a comparison between Example 7 and Comparative Example 3, it was proved that Example 7 could maintain the effect of controlling the release of a fertilizer component for a longer period of time than that in Comparative Example 3, even though the production time of Example 7 was shorter than that of Comparative Example 3.

The invention claimed is:

1. A method for producing coated water-soluble particles in a manner to form two or more coating layers on surfaces of water-soluble particles, comprising:

bringing water-soluble particles into a rolling state in a rotary pan or a tumbler, thereafter supplying a first coating material that comprises a polyol component and an isocyanate component to provide first coating bodies that have coating layers formed of the first coating material that has not been sufficiently cured, while maintaining the rolling state of the water-soluble particles, and thereafter additionally supplying a second coating material to surfaces of the first coating bodies to provide second coating bodies that have coating layers of the second coating material, while maintaining the rolling state of the water-soluble particles, wherein supplying the second coating material starts within a time range represented by $T_x$ that satisfies the following relational expression:

$$0.5 \le (T_x - T_0)/(T_a - T_0) \le 3.0,$$

wherein $T_0$ is a time at which, after finishing supplying the first coating material, the first coating bodies begin adhering to each other to form aggregated particles and $T_a$ is a time at which the volume of the aggregated particles reaches a maximum.

2. A method for producing coated water-soluble particles as claimed in claim 1, wherein the supplying steps are repeated two to ten times to form two to ten coating layers.

3. A method for producing coated water-soluble particles as claimed in claim 1, wherein the second coating material comprises a polyol component and an isocyanate component.

4. A method for producing coated water-soluble particles as claimed in claim 1, wherein supplying the second coating material starts within a time range represented by $T_x$ that satisfies the following relational expression:

$$0.5 \le (T_x - T_0)/(T_a - T_0) \le 2.0.$$

5. A method for producing coated water-soluble particles as claimed in claim 1, wherein the first coating material and the second coating material comprise an amine compound.

6. A method for producing coated water-soluble particles as claimed in claim 1, wherein the mass of the coating layers, per one layer, is 0.5 to 5 mass % relative to the mass of the coated water-soluble particles.

7. A method for producing coated water-soluble particles as claimed in claim 1, wherein the coated water-soluble particles have a particle diameter of between 1 and 10 mm.

8. A method for producing coated water-soluble particles as claimed in claim 1, wherein the supplying steps are conducted continuously.

* * * * *